US006190883B1

(12) United States Patent
Srivastava et al.

(10) Patent No.: US 6,190,883 B1
(45) Date of Patent: Feb. 20, 2001

(54) METHOD FOR THE PRODUCTION OF HETEROLOGOUS POLYPEPTIDES IN TRANSFORMED YEAST CELLS

(75) Inventors: Aradhana Srivastava, Kanpur (IN); Jure Piskur, Copenhagen (DK); Jens Nielsen, Charlottenlund (DK); Michi Egel-Mitani, Vedbæk (DK)

(73) Assignee: Novo Nordisk A/S, Bagsvaerd (DK)

( * ) Notice: Under 35 U.S.C. 154(b), the term of this patent shall be extended for 0 days.

(21) Appl. No.: 09/392,126

(22) Filed: Sep. 8, 1999

Related U.S. Application Data
(60) Provisional application No. 60/101,524, filed on Sep. 23, 1998.

(30) Foreign Application Priority Data
Sep. 9, 1998 (DK) ................................................ 01131/98
Jan. 18, 1999 (DK) ................................................ 00052/99

(51) Int. Cl.[7] ............................... C12P 21/06; C12N 1/14
(52) U.S. Cl. ..................................... 435/69.1; 435/254.21
(58) Field of Search ................................. 435/69.1, 243, 435/254.21; 424/93.21

(56) References Cited

U.S. PATENT DOCUMENTS

| | | | |
|---|---|---|---|
| 5,316,923 | 5/1994 | Christiansen | 435/69.9 |
| 5,753,487 | 5/1998 | Eigtved et al. | 435/232 |
| 5,770,406 | 6/1998 | Kofod et al. | 435/74 |
| 5,770,424 | 6/1998 | Outtrup et al. | 435/200 |
| 5,783,416 | 7/1998 | Thim et al. | 435/69.1 |

FOREIGN PATENT DOCUMENTS

| | | |
|---|---|---|
| WO 95/02043 | 1/1995 | (WO) . |
| WO 96/28542 | 9/1996 | (WO) . |
| WO 97/32014 | 9/1997 | (WO) . |
| WO 97/33984 | 9/1997 | (WO) . |
| WO 98/01535 | 1/1998 | (WO) . |
| WO 98/13479 | 4/1998 | (WO) . |
| WO 98/26079 | 6/1998 | (WO) . |
| WO 98/32867 | 7/1998 | (WO) . |

OTHER PUBLICATIONS

Hiro–aki Fujimura, FEMS Microbiology Letters, vol. 82, pp. 149–152 (1991).
van Dijken et al., Antonie van Leeuwenhoek, vol. 63, pp. 343–352 (1993).
Inomata et al., Journal of Bacteriology, vol. 176, No. 15, pp. 4770–4773 (Aug. 1994).
Van Urk et al., Applied and Environmental Microbiology, vol. 56, No. 1, pp. 281–287 (Jan. 1990).
Romanos et al., Yeast 8: 423–488, Foreign gene expression in yeast: a review, 1992.*

* cited by examiner

*Primary Examiner*—Robert A. Schwartzman
*Assistant Examiner*—Katharine F. Davis
(74) *Attorney, Agent, or Firm*—Steve T. Zelson, Esq.; Valeta A. Gregg, Esq.

(57) ABSTRACT

The invention describes industrial fermentation of a Saccharomyces yeast species for production of a heterologous product encoded by a plasmid or DNA contained in said Saccharomyces yeast species which method utilizes the substrate more efficiently and without fermentative metabolism resulting in formation of ethanol and other unwanted primary products of fermentative activity whereby high yields of the heterologous product are obtained. The Saccharomyces yeast species is preferably a Crabtree negative Saccharomyces species in particular *Saccharomyces kluyveri*.

7 Claims, 6 Drawing Sheets

BATCH FERMENTATION PROFILE OF S. KLUYVERI GRY1183

EXIT GAS PROFILE DURING FERMENTATION OF S. KLUYVERI GRY1183

FIG 1A: BATCH FERMENTATION PROFILE OF
S. KLUYVERI GRY1183

FIG 1B: EXIT GAS PROFILE DURING FERMENTATION OF S. KLUYVERI GRY1183

FIG 2A: BATCH FERMENTATION PROFILE OF
S. KLUYVERI GRY1175

FIG 2B: EXIT GAS PROFILE DURING FERMENTATION OF S. KLUYVERI GRY1175

FIG 3A: PROTEINASE A PRODUCTION IN BATCH FERMENTATION IN OPTIMISED MEDIUM USING S. KLUYVERI AS57 STRAIN

FIG 3B: GAS ANALYSER READING FOR CARBON DIOXIDE PRODUCTION DURING BATCH PROTEINASE A PRODUCTION USING S. KLUYVERI AS57 STRAIN

METHOD FOR THE PRODUCTION OF HETEROLOGOUS POLYPEPTIDES IN TRANSFORMED YEAST CELLS

This application claims priority under 35 U.S.C. 119 of Danish application Nos. PA 1998 01131 filed Sep. 9, 1998, PA 1999 00052 filed Jan. 18, 1999. Priority is also claimed to U.S. Provisional application No. 60/101,524 filed on Sep. 23, 1998, the contents of which are fully incorporated herein by reference.

FIELD OF THIS INVENTION

The present invention is related to a method for the production and secretion of heterologous proteins or polypeptides in Crabtree negative Saccharomyces yeast species, and DNA-sequences, vectors and transformed cell lines for use in such method.

BACKGROUND OF THIS INVENTION

*Saccharomyces cerevisiae* is an attractive organism for heterologous protein production and many suitable expression systems have been developed to produce high level of proteins with this organism. This yeast is also the best studied eukaryotic organism and many molecular tools have been developed. However, *S. cerevisiae* has some limitations in its commercial application, due to its relatively poor secretion efficiency of proteins, the need to use fed-batch fermentation techniques to attain high cell densities and hence improve the protein synthesis, and secretion of O- and N-glycosylated proteins which are often hyperglycosylated. Although, *S.cerevisiae* is regarded as a very proteolysis weak host organism, a further problem encountered in production of some heterologous proteins in *S. cerevisiae* is low yield, presumably due to proteolytic processing both in intracellular compartments and at the plasma membrane cf. Gabrielsen et al. Gene, 90:255–262, 1990, (secretion of human parathyroid hormone by *S. cerevisiae*), Rokkones et al., J. Biotechnol. 33:293–306 (secretion of human parathyroid hormone by *S. cerevisiae*), and Bitter et al. Proc. Natl. Acad. Sci. USA, 81:5330–5334, 1984 (secretion of β-endorphine by *S. cerevisiae*).

According to Waldron and Lacroute, J. Bacteriol., 122:855–865,1975, the protein synthesis rate in yeast is dependent on the specific growth rate. They demonstrated that the net rate of protein synthesis in yeast lowered with decreasing specific growth rate. This was due to the decrease in average ribosomal efficiency i.e. the rate of protein synthesis per ribosome.

In batch culture with glucose as the carbon and energy source, the yeast *S. cerevisiae* will mainly ferment glucose to ethanol. Under anaerobic conditions, this is the only mode of energy production. In the presence of oxygen respiration occurs. However, alcoholic fermentation may s et in even under aerobic conditions if the glucose concentration surpasses a critical threshold value (Verduyn et al, J. Microbiol. Methods, 2:15–25, 1984; and vanDijken and Scheffers, FEMS Microbiol. Review, 32:199–244, 1986). This affects the biomass yield drastically (Reiger et al, J. Gen. Microbiol., 129:653–661, 1983; and von Meyenburg, Arch. Microbiol., 66:289–303, 1969). At the level of pyruvate, respiration competes with alcoholic fermentation via the mitochondrial pyruvate dehydrogenase complex and the cytosolic pyruvate decarboxylase. Acetaldehyde formed by the activity of pyruvate decarboxylase can after oxidation to acetic acid enter the tricarboxylic acid (TCA) cycle via acetyl CoA. Alternatively, acetaldehyde may be reduced to ethanol instead of being oxidized to carbon dioxide. *S. cerevisiae* can secrete all its fermentive metabolites acetate, pyruvate, ethanol, glycerol and succinate in glucose limited aerobic batch fermentation.

The overflow metabolism and repression of respiration in yeast strains resulting in redirection of substrate towards fermentative metabolism resulting in formation of ethanol and other primary products of fermentative activity, is referred to as the "Crabtree effect". This effect is remarkable in the species *Saccharomyces cerevisiae*. However, so far it has not been clear what the situation is with other species belonging to the genus Saccharomyces. Presently the genus Saccharomyces consists of more than ten species (Piskur, J. et al Int. J. System. Bacteriol. 48:1015–1024, 1998).

In literature, most of the yeast species employed for heterologous protein expression like *Kluveromyces lactis*, *Pichia pastoris*, *Hansenuela polymorpha*, *Schwanniomyces occidentalis* and *Yarrowia lipolytica*, are not respiration-limited yeasts (Kreger-van Rij, Classification of yeasts, in Yeast vol 1:5–66, 1987 and Heslot et. al., J. Bacteriol., 104:473–491, 1970). These strains differ from *S. cerevisiae* in being Crabtree negative yeast strains, thus having the advantage of utilizing the substrate more efficiently for protein and biomass synthesis. However, from a molecular biology aspect these yeast strains are not very well characterized and they are not as easy to manipulate as *S. cerevisiae*. Moreover, the secretion properties of these yeast strains are not characterized as well as for *S. cerevisiae*.

The present invention is based on the surprising recognition by the inventors hereof that at least one Saccharomyces species, namely *Saccharomyces kluyveri* is Crabtree negative or is only effected in a very small degree by glucose surplus during aerobic batch fermentation. *S. kluyveri* is a distant relative of *S. cerevisiae* and showed higher biomass yield on glucose than *S. cerevisiae* in batch fermentation confirming its higher respiratory capacity over *S. cerevisiae*. This is a desirable feature for the protein biosynthesis. FIG. 1*a*, 1*b*, 2*a* and 2*b* clearly demonstrate that the *Saccharomyces kluyveri* strains are "Crabtree negative".

SUMMARY OF THE INVENTION

The present invention is related to an industrial Saccharomyces yeast fermentation method for production of a heterologous product encoded by a plasmid or DNA contained in said strain which method utilizes the substrate more efficiently and without or with reduced fermentative metabolism resulting in formation of ethanol and other unwanted primary products of fermentative activity whereby high yields of the heterologous product are obtained.

The invention is related to a method for producing a heterologous product comprising (a) cultivation under industrial conditions a Saccharomyces yeast strain which comprises a plasmid or DNA encoding the protein wherein the strain utilizes the substrate more efficiently and has less or no fermentative metabolism and (b) recovering the protein.

More specifically the present invent ion is related to an industrial fermentation method comprising culturing a Crabtree negative Saccharomyces yeast species in a suitable culture medium said Crabtree negative yeast species comprising DNA coding for the desired product operably linked to transcriptional and translational control sequences and other sequences necessary for expression in yeast whereupon the expressed product is isolated from either the cells or the culture medium.

In a preferred embodiment of the present invention the Crabtree negative Saccharomyces species is *Saccharomyces kluyveri*.

The transcriptional and translational control sequences may preferably be derived from *Saccharomyces cerevisiae* genes, from *Saccharomyces kluyveri* genes or from genes from both species.

By "Crabtree negative yeast species" in this context is meant that the yeast strain produces no or a substantially lowered amount of ethanol than *S. cerevisiae* under aerobic condition irrespective of the mode of cultivation (growth under sugar limitation or growth with excess sugar).

By "a substantially lowered amount of ethanol produced" is meant that less than 10 mg ethanol is formed per g glucose taken up by the cells when *S. kluyveri* GRY1175 and GRY1183 are cultured in the medium given by Verduyn et al. in 1990 or in optimized medium (see Example 1). Preferably the amount of ethanol produced should be less than 5 mg per g glucose, more preferably the amount should be less than 2.5 mg per g glucose and even more preferred it should be zero.

With "excess sugar" is meant up to 40 g/liter of glucose present in Verduyn medium or present in the optimized medium (see Example 1).

By "reduced fermentative metabolism" or "less or no fermentative metabolism" is meant that the amount of ethanol produced per g glucose during fermentation is at least 25% reduced as compared to that observed in *S. cerevisiae* under same substrate concentration strain which is about 0.3 g ethanol/g glucose. The reduction will typically be at least 50%. It is preferred that the reduction is at least 75% and even better at the least 90% or 95%.

With "industrial fermentation" or "under industrial conditions" is meant production scale higher than 10 $m^3$, preferably between 10 and 500 $m^3$, more preferably between 50 and 200 $m^3$ and even more preferably between 80 and 180 $m^3$.

In still a further aspect, the present invention is related to an industrial Saccharomyces yeast fermentation method for production of a heterologous product encoded by a plasmid or DNA contained in said strain wherein the fermentation time is shorter than the fermentation time for making the same amount of said heterologous product in *Saccharomyces cerevisiae*.

With "fermentation time" is meant the time from inoculation of the main fermentor to the time where further growth arrest because of limitation in one of the essential substrates, usually glucose.

In still a further aspect, the present invention is related to an industrial Saccharomyces yeast continuous fermentation method for production of heterologous product encoded by a plasmid or DNA contained in said strain wherein the dilution rate D is higher than 0.1 $h^{-1}$. The dilution rate is preferably between 0.15 $h^{-1}$ and 0.5 $h^{-1}$, and more preferably between 0.2 $h^{-1}$ and 0.3 $h^{-1}$.

The dilution rate D is defined as F/V where F is the substrate feed rate (volume per hour) and V is the volume of the culture medium in the fermenter.

High dilution rates are very desirable for a continues fermentation in industrial scale because they increases the fermentation capacity, i.e. the fermentation capacity is proportional to the dilution rate. As modern fermentation equipment is very costly this character is essential for a good production economy.

BRIEF DESCRIPTION OF THE DRAWINGS

The present invention will be described in further details by reference to the drawings in which.

DETAILED DESCRIPTION OF THE INVENTION

Figure 1A:
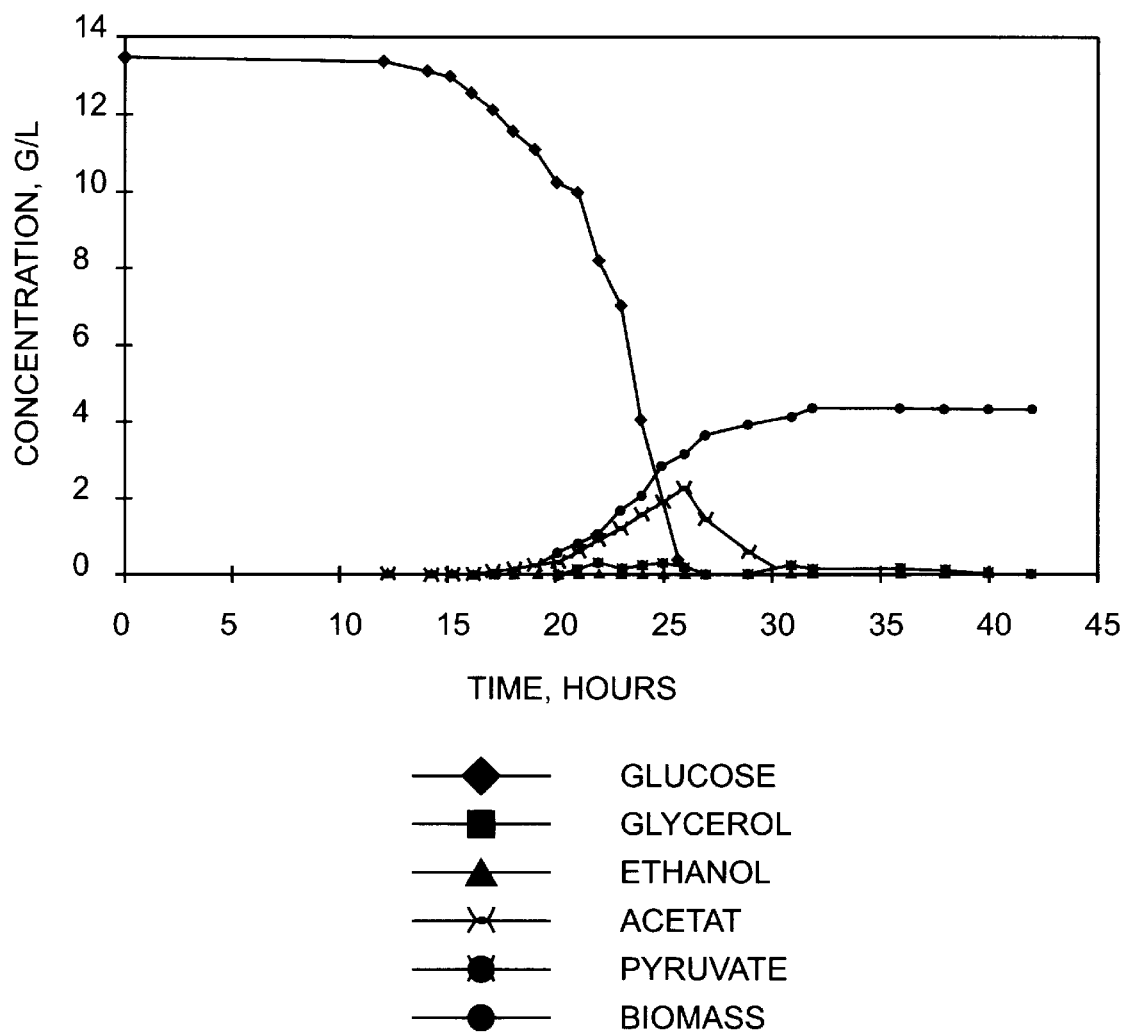
FIG. 1a and 1b show batch fermentation profile of *S. kluyveri* GRY1183 strain along with the exit gas profile during fermentation.
Figure 1B:
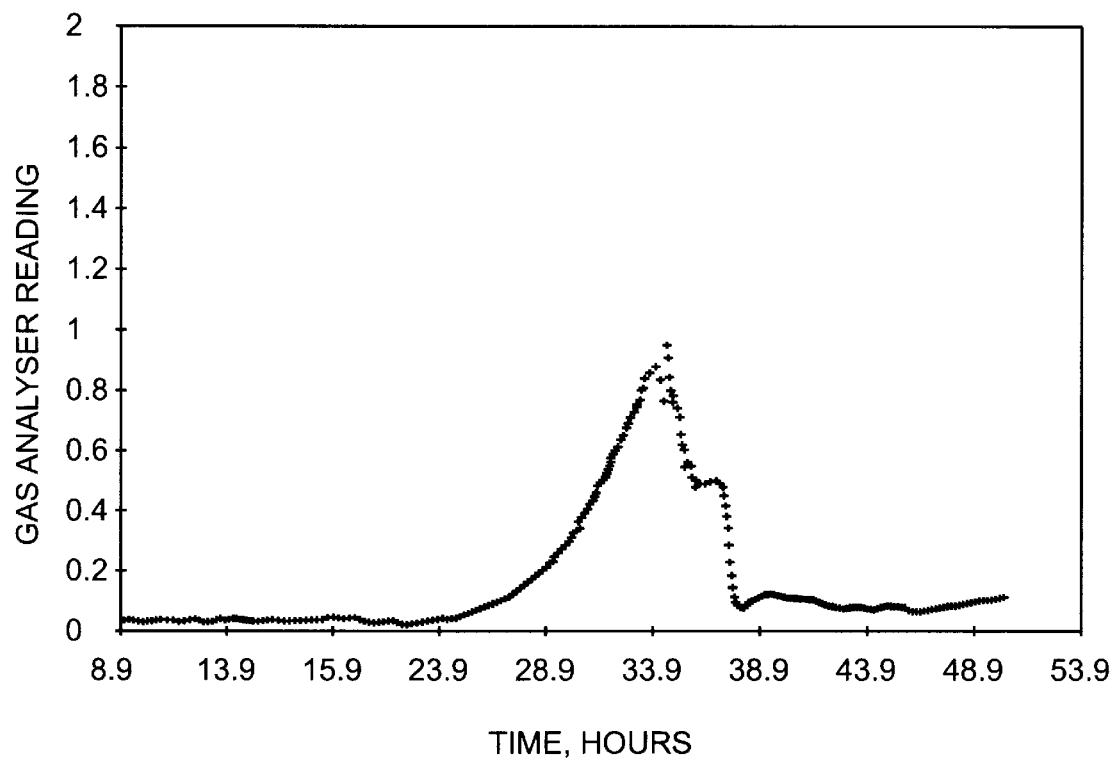

This invention describes the use of yeast strains within the Saccharomyces genus being a Crabtree negative yeast for expression of heterologous proteins in high yields. As an example proteinase A, a *S. cerevisiae* protein expressed by the PEP4 gene, was successfully expressed and secreted in *Saccharomyces kluyveri*. The recombinant strains were obtained by transformation with the $2\mu$ based plasmid derived from *S. cerevisiae*. Stable maintenance of plasmid bearing cell population was ensured through a selection strategy mechanism, that could depend on the completion of an auxotrophic marker such as the URA3 or TPI1 marker or the introduction of a suitable antibiotic resistance gene such as kanamycin G418 from *E. coli* or neomycin. Thereby stable recombinant *S. kluyveri* strains for production and secretion of biologically active heterologous protein were developed. Furthermore, the efficient performance of these recombinant strains in batch fermentations was demonstrated.

The present invention also discloses an expression vector for expression and secretion of an insulin precursor MI3 with the structure B(1-29)-Ala-Ala-Lys-A(1-21) where B(1-29) is the B chain of human insulin lacking the amino acid residue in position B(30) and A(1-21) is the A chain of human insulin. The vector contains the MI3 encoding DNA linked in proper reading frame with the signal/leader sequence from the MFαS.k. gene under transcriptional control of the MFαS.k promoter.

*S. kluyveri* was found as a Crabtree negative yeast having the advantage of biosynthesizing more biomass/proteins than other Saccharomyces yeasts. It is also capable of secreting its own and heterologous proteins. Although, *S. kluyveri* being different from *S. cerevisiae* in its genomic structure, it can stably accommodate *S. cerevisiae* based (YEp24) plasmids. The strain is also capable of secreting heterologous proteins with the same immunological and enzyme activity as that observed in *S. cerevisiae*. The present invention thus demonstrates that Crabtree negative Saccharomyces yeast species, such as *S. kluyveri*, are interesting alternatives to the Crabtree positive *S. cerevisiae* for expressing heterologous peptides or proteins.

The preferred host should grow fast and accommodate the plasmid vector freely for high level expression of heterologous genes. Besides these properties, such strain should also exhibit high maximum specific growth rate, and least pronounced "Crabtree effect" in a batch fermenter. The present invention demonstrates that *S. kluyveri* NRRL-Y-12651 and IFO 1894 were capable of utilizing the glucose substrate most efficiently for protein and biomass synthesis at high maximum specific growth rate. These *S.kluyveri* strains were found to be superior to *S. cerevisiae* strains when their growth yields on glucose were compared in a batch fermenter.

Definitions

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, New York. The DNA constructs may be prepared synthetically by established standard methods, e.g. the phosphoamidite method described by S. L. Beaucage and M. H. Caruthers, *Tetrahedron Letters* 22, 1981, pp. 1859–1869, or the method described by Matthes et al., *EMBO Journal* 3, 1984, pp. 801–805. According to the phosphoamidite method, oligonucleotides are synthesized, e.g. in an automatic DNA synthesizer, purified, duplexed and ligated to form the synthetic DNA construct. A currently preferred way of preparing the DNA construct is by polymerase chain reaction (PCR), e.g. as described in Sambrook et al., *Molecular Cloning: A Laboratory Manual,* Cold Spring Harbor, N.Y., 1989).

Expression Vector

An expression vector is a DNA molecule, linear or circular, that comprises a segment encoding a polypeptide of interest operably linked to additional segments that provide for its transcription. Such additional segments may include promoter and terminator sequences, and optionally one or more origins of replication, one or more selectable markers, an enhancer, a polyadenylation signal, and the like. Expression vectors are generally derived from plasmid or viral DNA.

Transcriptional and translational control sequences are DNA regulatory sequences, such as promoters, enhancers, terminators, and the like, that provide for the expression of a coding sequence in a host cell. Each control sequence may be native or foreign to the nucleic acid sequence encoding the polypeptide. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

Signal Sequence

A "signal sequence" is a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The secretory signal sequence may encode any signal peptide which ensures efficient direction of the expressed polypeptide into the secretory pathway of the cell. The signal peptide may be a naturally occurring signal peptide, or a functional part thereof, or it may be a synthetic peptide. Useful signal peptides for yeast host cells are obtained from the genes for *Saccharomyces cerevisiae* MFα-factor and *Saccharomyces cerevisiae* invertase, the signal peptide of mouse salivary amylase (cf. O. Hagenbuchle et al., Nature 289, 1981, pp. 643–646), a modified carboxypeptidase signal peptide (cf. L. A. Valls et al., Cell 48, 1987, pp. 887–897), the yeast BAR1 signal peptide (cf. WO 87/02670), or the yeast aspartic protease 3 (YAP3) signal peptide (cf. M. Egel-Mitani et al., Yeast 6, 1990, pp. 127–137). Further useful signal peptides may be derived from *S. kluyveri* secreted polypeptides such as MFα$^{s.k.}$. Other useful signal peptide coding regions are described by Romanos et al., Yeast 8:423–488,1992.

For efficient secretion in yeast, a sequence encoding a leader peptide may also be inserted downstream of the signal sequence and upstream of the DNA sequence encoding the desired polypeptide. The function of the leader peptide is to allow the expressed polypeptide to be directed from the endoplasmic reticulum to the Golgi apparatus and further to a secretory vesicle for secretion into the culture medium (i.e. exportation of the polypeptide across the cell wall or at least through the cellular membrane into the periplasmic space of the yeast cell). The leader peptide may be the yeast MFα-factor leader (the use of which is described in e.g. U.S. Pat. No. 4,546,082, EP 16 201, EP 123 294, EP 123 544 and EP 163 529). Alternatively, the leader peptide may be a synthetic leader peptide that is a leader peptide not found in nature. Examples of such synthetic leader peptides are described in WO 89/02463 or WO 92/11378.

Promoters

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes. The promoter may be any nucleic acid sequence which shows transcriptional activity in the host cell of choice and may be obtained from genes encoding extracellular or intracellular polypeptides either homologous or heterologous to the host cell.

Suitable promoters from *S. cerevisiae* genes include the MFα1 promoter, galactose inducible promoters such as GAL1, GAL7 and GAL10 promoters, glycolytic enzyme promoters including TPI and PGK promoters, TRP1 promoter, CYCI promoter, CUP1 promoter, PHO5 promoter, ADH1 promoter, and HSP promoter. Useful promoters from *S. kluyveri* include the invertase promoter and promoters from glycolytic and respiratory genes. Other useful promoters for yeast host cells are described by Romanos et al., 1992, Yeast 8:423–488.

"Operably linked", when referring to DNA sequences, indicates that the sequences are arranged so that they function in concert for their intended purposes, e.g. transcription initiates in the promoter and proceeds through the coding segment to the terminator.

Terminators

The terminator sequence is operably linked to the 3' terminus of the nucleic acid sequence encoding the desired polypeptide. Any terminator which is functional in the host cell of choice may be used in the present invention. Preferred terminators will be derived from the genes encoding *Saccharomyces cerevisiae* enolase, *Saccharomyces cerevisiae* cytochrome C (CYC1), or *Saccharomyces cerevisiae* glyceraldehyde-3-phosphate dehydrogenase, triosephosphate isomerase and mating factor MFα1, or from *S. kluyveri* glycolytic and respiratory genes. Other useful terminators for yeast host cells are described by Romanos et al., 1992, supra.

Polyadenylation Signals

Useful polyadenylation sequences for yeast host cells are described by Guo and Sherman, 1995, *Molecular Cellular Biology* 15:5983–5990.

The recombinant expression vectors will comprise a nucleic acid sequence encoding the desired product, a promoter, and transcriptional and translational stop signals. The various nucleic acid and control sequences described above may be joined together to produce a recombinant expression vector which may include one or more convenient restriction sites for further modification. Alternatively the nucleic acid sequence encoding the desired product may be expressed by inserting the nucleic acid sequence into an appropriate vector for expression. In creating the expression vector, the coding sequence is located in the vector so that the coding sequence is operably linked with the appropriate control sequences for expression, and possibly secretion.

The recombinant expression vector may be any vector (e.g., a plasmid or virus) which can be conveniently subjected to recombinant DNA procedures and can bring about the expression of the nucleic acid sequence. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. The vector system may be a single vector or plasmid or two or more vectors or plasmids which together contain the total DNA to be introduced into the genome of the host cell, or a transposon.

The vector will preferably contain one or more selectable markers which permit easy selection of transformed cells. A selectable marker is a gene the product of which provides for biocide or viral resistance, resistance to heavy metals, prototrophy to auxotrophs, and the like. Suitable markers for yeast host cells are ADE2, HIS3, LEU2, LYS2, MET3, TRP1, URA3, TPI1, PGK and geneticin G418$^R$ by the KAN$^{E.c.}$ gene.

For autonomous replication, the vector may further comprise an origin of replication enabling the vector to replicate autonomously in the yeast host. Examples of origin of replications for use in a yeast host cell are the 2 micron origin of replication, the combination of CEN6 and ARS4, and the combination of CEN3 and ARS1. The origin of replication may be one having a mutation which makes its functioning temperature-sensitive in the host cell (see, e.g., Ehrlich, 1978, Proceedings of the National Academy of Sciences USA 75:1433).

More than one copy of a nucleic acid sequence encoding a polypeptide of the present invention may be inserted into the host cell to amplify expression of the nucleic acid sequence. Stable amplification of the nucleic acid sequence can be obtained by integrating at least one additional copy of the sequence into the host cell genome using methods well known in the art and selecting for transformants.

The procedures used to ligate the elements described above to construct the recombinant expression vectors of the present invention are well known to one skilled in the art (see, e.g., Sambrook et al., 1989, supra).

The yeast strain may be transformed using the procedures described by Becker and Guarente, In Abelson, J. N. and Simon, M. I., editors, Guide to Yeast Genetics and Molecular Biology, Methods in Enzymology, Volume 194, pp 182–187, Academic Press, Inc., New York; Ito et al., 1983, Journal of Bacteriology 153:163; and Hinnen et al., 1978, Proceedings of the National Academy of Sciences USA 75:1920.

The transformed host cells are then cultured for a sufficient time and under appropriate conditions known to those skilled in the art in view of the teachings disclosed herein to permit the expression and secretion of the desired product.

Throughout the description and claims is used one and three letter codes for amino acids in accordance with the rules approved (1974) by the IUPAC-IUB Commission on Biochemical Nomenclature, vide Collected Tentative Rules & Recommendations of the Commission on Biochemical Nomenclature IUPAC-IUB, 2nd ed:, Maryland, 1975.

Products which can be produced by the present invention are insulin and insulin analogs, glucagon, aprotenin, GLP1, IGF1, HBP, GSF, adrenocorticotropic hormones, angiotensinogen, atrial natriuretic peptides, dynorphin, endorphines, galanin, gastrin, gastrin releasing peptides, neuropeptide Y fragments, pancreastatin, pancreatic polypeptides, secretin, vasoactiv intestinal peptide, growth hormone releasing factor, melanocyte stimulating hormone, neurotensin, adrenal peptide, parathyroid hormone and related peptides, somatostatin and related peptides, brain natriuretic peptide, calcitonin, corticotropin releasing factor (CRF), thymosin and urotensin; and homologous or otherwise related peptides and fragments of these and other polypeptides as subtilisins, trypsins, carbohydrases, oxidases, transglutaminases and other enzymes of prokaryotic or eukaryotic origins.

The present invention is further illustrated by the following examples which, however, are not to be construed as limiting the scope of protection. The features disclosed in the fore-going description and in the following examples may, both separately and in any combination thereof, be material for realizing the invention in diverse forms thereof.

The design and operation of a typical fermentor is described in Bailey & Ollis, Biochemical Engineering Fundamentals, p620–26, Sec.ed. 1986, McGraw-Hill, ISBN O-07-003212-2A. The operation is traditionally divided between batch, i.e. all ingredients added before inoculation, fed batch where a limiting nutrient is added during the fermentation to derepress a promoter, prevent ethanol formation, limit growth rate, etc., finally the operation can be continuous which means that at a constant feed of complete medium is fed to the fermentor and an equal amount of culture medium is removed from the fermentor as described in Aiba, Humphey and Millis: Biochemical Engineering, Academic Press N.Y., 1965.

EXAMPLE 1

Expression of *Saccharomyces cerevisiae* Proteinase A in *S. kluyveri* Strains

Strains and Culture Conditions

Saccharomyces yeast type isolates *S. kluyveri* NRRL-Y-12651$^T$ and *S. cerevisiae* X2180-1A were used for batch fermentation studies. The NRRL.Y strain originates from the National Center for Agricultural Utilization Research, Peoria, Ill., USA. The auxotrophic haploid strains of *S. kluyveri,* GRY1175 MATα, ura3$^-$ and GRY1183 MATa, ura3$^-$, were employed for transformation with two YEp24 plasmids pPA2 and pJW1103. The strains GRY1175 and GRY1183 were supplied by J. Strathern, National Institute of Cancer, FCRDC, Frederick, Md., USA. The industrial strain *S. cerevisiae* JG176 was used for comparison. This strain is *S. cerevisiae* MT 663 (MATa/MATα, leu2leu2, pep4-3/pep4-3, HIS4/his4, tpi::LEU2/ tpi::LEU2, cir$^+$) transformed with the plasmid pYJLP-P10 coding for the PEP4$^{S.c.}$ promoter and gene and the TPI1$^{S.c.}$ terminator and also carrying the TPI gene from *S. pombe* for selection on glucose media and the pBR322 origin and amp$^R$ gene for propagation in *E. coli* (Jochumsen K., "Production of Proteinase A by *S. cerevisiae*", PhD Thesis, Technical University of Denmark, 1995).

The strain *Escherichia coli* DH5α was used for plasmid preparation work.

The strains including transformants (see Table 1) were maintained in minimal medium (2% glucose, 1% succinic acid, 0.6% sodium hydroxide and 0.67% yeast nitrogen base) with and without uracil in agar plates and stored at −80° C. Before every fermentation, the frozen culture was transferred to fresh medium plates and then to the fermentation medium for inoculum preparation. Proteinase A activity in the culture was tested on the milk plates (2% glucose, 1% yeast extract, 0.5% peptone and 2% skimmed milk).

TABLE 1

Recombinant strains of *S. kluyveri* used in this example

| Transformants | Host strain | Genotype | Plasmid | Proteinase A yields, mg/g glucose* |
|---|---|---|---|---|
| *S. kluyveri* AS110 | *S. kluyveri* GRY1175 | MATα ura3 | pPA2 | 0.42 |
| *S. kluyveri* AS23 | *S. kluyveri* GRY1175 | MATα ura3 | pJW1103 | 0.19 |
| *S. kluyveri* AS43 | *S. kluyveri* GRY1183 | MATa ura3 | pPA2 | 0.23 |
| *S. kluyveri* AS57 | *S. kluyveri* GRY1183 | MATa ura3 | pJW1103 | 0.83 |

*In medium given by Verduym et al. 1990

Plasmids

Two 2μ based plasmids pPA2 (13.309 Kb) and pJW1103 (11.8 Kb) were used for transformation. These plasmids were generous gifts from Jakob Winther, Yeast Genetic Department, Carlsberg Laboratory, Denmark and used in earlier studies (Soerensen et al., Europ. J. Biochem., 220:19–24, 1994; and Rothman et al., Proc. Natl. Acad. Scin., 83:3248–52, 1986). They contain the *S. cerevisiae* PEP4 gene under regulation of its own promoter. The PEP4 gene of *S. cerevisiae* encodes the vacuolar aspartic protease proteinase A.

Proteinase A is secreted to the medium when overexpressed from a multicopy plasmid in *S. cerevisiae* (Stevens, T. H. et al., J. Cell. Biol. 102,1551–1557 (1986).

POT selection could be carried out in *S. kluyveri* by deletion of the *S. kluyveri* TPl1 gene using the same or related technique as used in *S. cerevisiae* MT663.

Transformation of Yeast Cells

Auxotrophic strains of *S. kluyveri* were transformed using a modified lithium acetate method (Ito et al., J. Bacteriol., 153:163–168, 1983) and plated on minimal medium without uracil. Only the plasmid containing cells synthesizing uracil for their growth, could grow in these plates. The corresponding colonies were retransferred to the YPD plates containing skimmed milk for testing their proteinase A secretion capacity. The halo appeared around the cell colonies indicating the expression of the PEP4 gene encoding proteinase A. In the non-transformed strains, i.e. NRRL-Y-12651, GRY1175 and GRY1183, there was no halo.

Southern Analysis

Total DNA from recombinant yeast strains was digested with restriction enzymes EcoRI and XbaI, electrophorised in 1% agarose gel, and vacuum blotted on Hybond N+ nylon membrane. The membrane was hybridized with the $p^{32}$ labeled plasmids pPA2 and pJW1103 obtained by the random priming method. For analysis of copy number, hybridization pattern was compared with the standard high copy strain containing the PEP4 gene (Jochumsen, K., PhD Thesis, Technical University of Denmark, 1995). The radioactivity of each single band was measured by an Instant Imager (Packard Instrument Company, Meriden).

Fermentation and Culture Conditions

An optimized carbon limited medium given by Verduyn et al. (J. Gen. Microbiol., 136:405–412, 1990) for *S. cerevisiae* and related yeasts was used for batch fermentation studies. This medium was supplemented with glucose (10 g.l$^{-1}$, for growth studies) and (40 g.l$^{-1}$, for heterologous protein production). All the batch studies were performed in 5 l (working volume 4 liters) batch fermenter (built in house), equipped with all monitors and controllers to maintain the agitation rate (800 rpm), aeration rate (1 v.v.m.), temperature (25±0.1° C.), and pH (6.0±0.1 for growth studies and 5.0±0.1 for Proteinase A production). The pH of the medium was maintained by the addition of 2N sodium hydroxide solution and 2N sulfuric acid solution. The samples were collected at different time intervals during the batch fermentations. For intracellular protein analysis, the cells were centrifuged, crushed with glass beads, and mixed with Laemmli buffer as described later in Protein electrophoresis and Immunoblott Analysis.

Analytical Methods

Dry Cell Weight Determination

The nitrocellulose filter paper (Gelma, pore size 0.45 micron) was mounted on watchglass plate with a piece of tissue paper between the glass and the filter, to avoid sticking of the filter to the glass surface. Then, the filter was dried in microwave oven for 10 min. at power setting of 15% (150w). Afterwards, it was cooled in a descicater for 15 minutes and weighed. 10 ml of the culture broth was filtered through the filter and the deposited cells on filter paper were washed with 10 ml of distilled water. Again, the filter was dried in the microwave oven for 15 min. and then cooled in descicater for 15 min. This filter with deposited dry cells was weighed again and the dry cell weight was measured by subtracting the weight of dry filter paper from it.

Substrate and Metabolites Concentrations

Extracellular metabolites were measured by filtering the fermentation broth immediately after sampling from fermenter, through cellulose acetate filters (Sartorious AG, Germany, pore size 0.45μ) and subsequently stored at −20° C. until analyzed. The substrate glucose and fermentation metabolites ethanol, glycerol, pyruvate, acetate, and succinate, were measured by high performance liquid chromatography (Waters, USA) using both differential refrectometer (Waters 410) and UV detector (Waters 486, adsorbance set at 210 nm). The HPX-87H column (Bio-Rad, California) with mobile phase (5 mM sulfuric acid solution in milli-Q water, flow rate 0.6 ml.min$^{-1}$), was used for extracellular sample analysis. The column temperature was maintained at 65° C.

Off-Gas Analysis

The concentration of the carbon dioxide and oxygen in the off gas was measured with a gas analyzer from Bruel and Kjær, Denmark. Samples were analyzed with 4 minutes intervals and recorded during the whole fermentation.

Proteinase A Assay

The proteinase A activity was measured using method described by Meldal and Breddam, Anal. Biochem., 195:141–147, 1991, and van den Hazel etal., Bio. Chem., 268:18002–7, 1993. The proteinase A activity and its concentration in extracellular medium was measured against standard Proteinase A (Sigma Chemicals, USA, catalogue number P8892).

Plasmid Stability Determination

The samples withdrawn at different time intervals during fermentation, were diluted using sterile distilled water, spread on YPD plates, and incubated for 2 days. These plates were replica plated on selective medium. The fraction of plasmid containing cells was measured by comparing growth on nonselective and selective plates.

Protein Electrophoresis and Immunoblot Analysis

The extracellular and intracellular protein compositions were analyzed by SDS-PAGE essentially as described by Laemmli, Nature, 227:680–685, 1970. SDS/PAGE was performed in 12% separation gels. The extracellular samples containing proteins were mixed with Laemmli buffer (0.1M Tris-HCl, pH 8.8/0.5M sucrose/5 mM EDTA/0.01% Bromophenol blue/2% SDS/4% 2-mercaptoethanol), incubated at 90° C. for 5 minutes and then incubated on ice for 5 minutes before loading it to the casted gels. Intracellular extracts were prepared using the method given by Piskur and Kielland-Brandt, Biotechnol. Appl. Biochem., 18:239–257, 1993. Cells separated from 1 ml of fermentation medium were washed with water and spun down. A volume of glass beads equal to that of pellet with 100 µl of the Laemmli buffer, was added. The suspension was mixed vigorously for 30 seconds, followed by 30 seconds incubation on ice, and the cycle was repeated several times to ensure the complete release of intracellular proteins. Afterwards, this sample was incubated at 90° C. for 5 minutes with subsequent cooling in ice for another 5 minutes before loading to the gel. The proteins were electrophoresised and then electroblotted on nitrocellulose filter. The pattern of the antigenic bands were developed with rabbit polyclonal anti-PrA antibody.

Proteinase A Production in Batch Fermentation

Batch fermentations were carried out using different transformed strains of S. kluyveri AS110, AS23, AS43 and AS57. These strains were tested for production of proteinase A in batch fermenters. The identification of these strains and the yields of proteinase A are given in Table 1. All strains were capable of producing proteinase A during the fermentation. To evaluate the potential of the transformed strains, an industrial strain S. cerevisiae JG176 was also studied for proteinase A production in batch fermenter under similar conditions. This strain is a high copy strain containing the S. cerevisiae PEP4 gene (see Jochumsen, K., 1995 as described earlier). The S. cerevisiae proteinase A produced by S. kluyveri AS57, was characterized by the SDS-PAGE analysis, its immunoactivity against rabbit polyclonal antibodies, and its ability to cleave the substrate specific for S. cerevisiae PrA. Proteinase A produced during fermentation of all transformants showed these three characteristics.

The stability of the transformed strains was also measured by replica plating method by measuring the plasmid bearing cells. This measure was high, 70–90%, and constant during the batch cultivation.

Out of the four competent strains tested, S. kluyveri AS57 was the best strain. This strain turned out to have a higher capability to utilize more carbon substrate in a given fermentation for biosynthesis of protein/biomass than S. cerevisiae JG176. In optimized medium, a batch cultivation resulted in overall proteinase A yield of 8 mg/g glucose with growth yield of 0.31 g/g glucose.

Figure 2A:
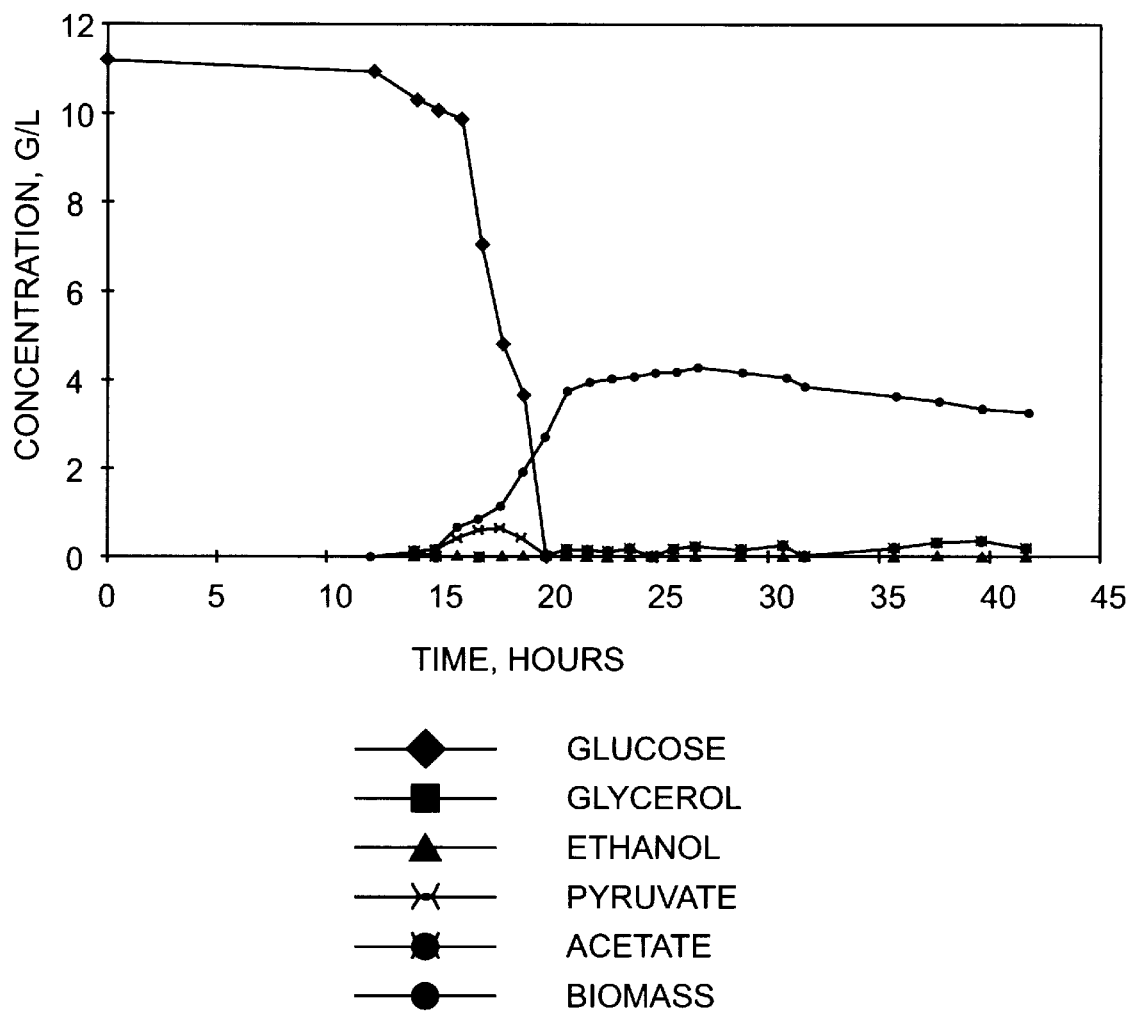
FIG. 2a and 2b show a batch fermentation profile of *S. kluyveri* GRY1175 strain along with the exit gas profile during fermentation.
Figure 2B:
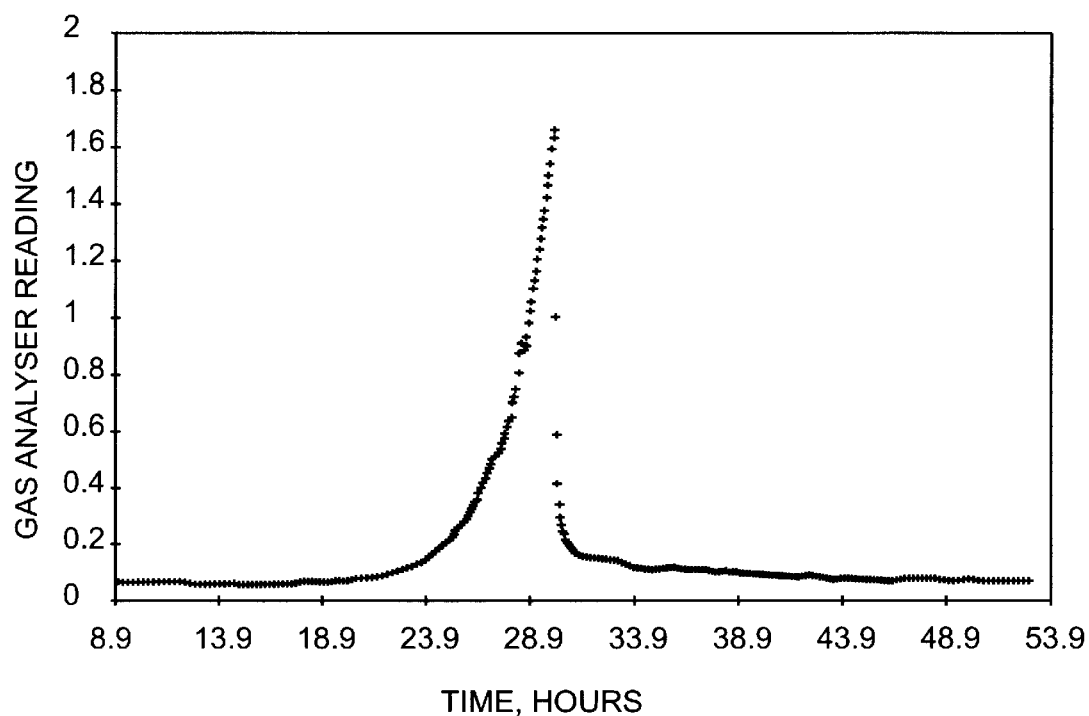
Figure 3A:
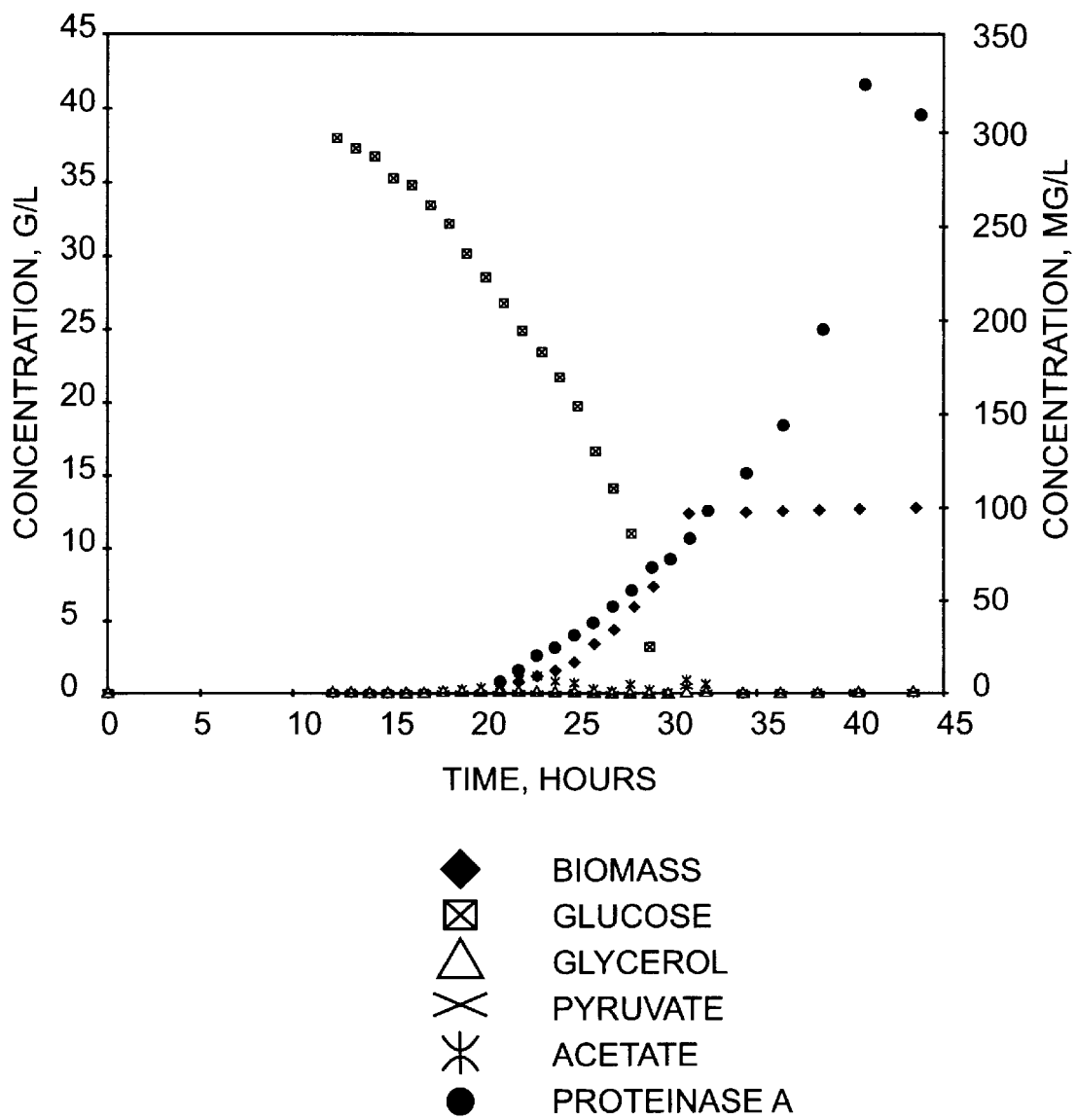
FIG. 3a shows batch proteinase A production profile.
Figure 3B:
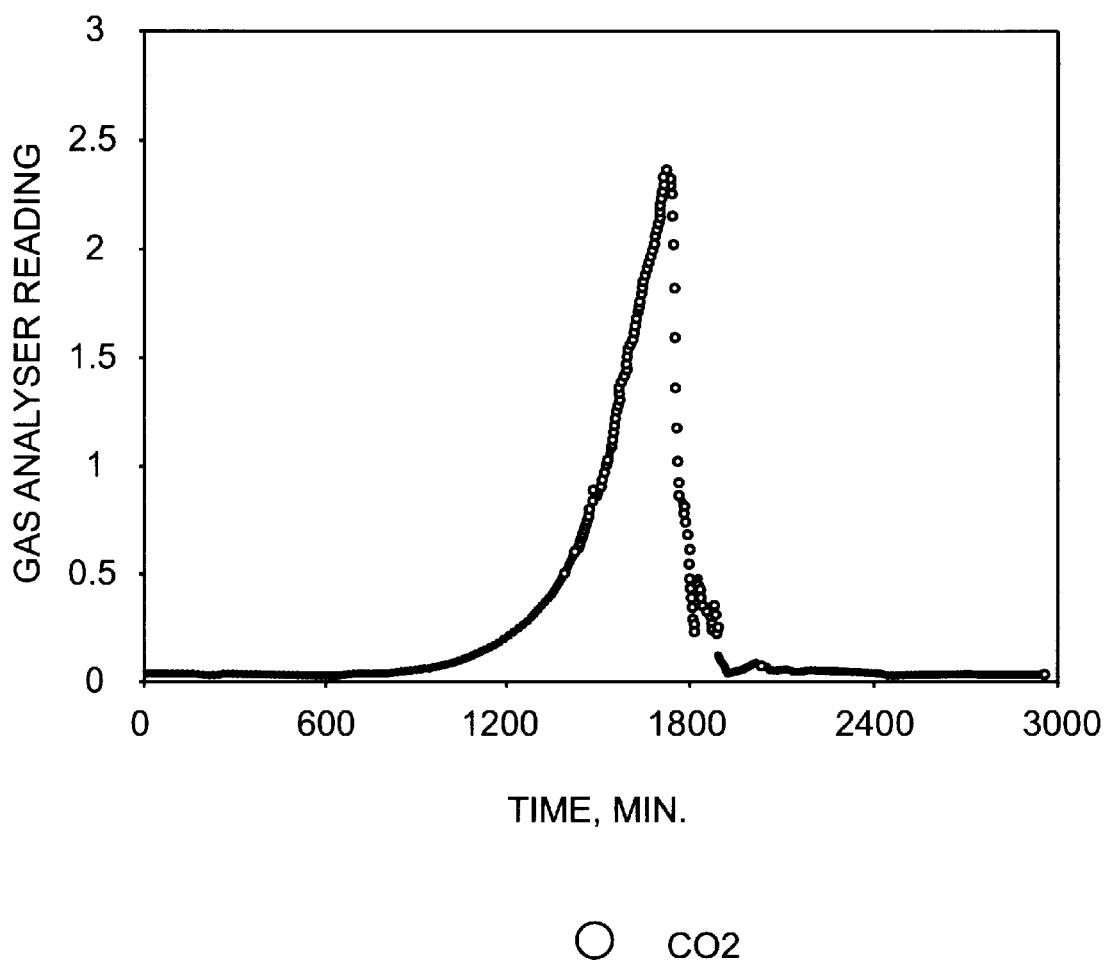
FIG. 3b shows the exit gas profile in optimized medium using *S. kluyveri* AS 57 strain.

The batch fermentation profiles of the developed recombinant strains of S. kluyveri AS57 (in optimized medium) along with their exit gas profile during fermentation is given in FIG. 2. S. kluyveri AS57 grew on glucose at maximum specific growth rate of $(0.35 \pm 0.02)$ $h^{-1}$. The maximum specific growth rate of the industrial strain of S. cerevisiae was observed as $(0.17 \pm 0.02)$ $h^{-1}$. The carbon dioxide in the exit gas also indicated that the S. kluyveri AS57 being a Crabtree negative yeast produced no ethanol during batch proteinase A production.

It appears from the above results that S. kluyveri AS 57 exhibits a higher maximum specific growth rate and a higher substrate utilization rate than S. cerevisiae. Because it is also able to secrete biologically active proteins (in casu proteinase A) it has a high potential for use as host for heterologous protein production.

In addition, the skim milk plate assay based on appearance of halo show that the proteolytic activity of S. kluyveri is very limited.

EXAMPLE 2

Investigation on the Effect of Different Phosphate Levels on Proteinase A Production The effect of phosphate level present in the fermentation medium on the proteinase A production, was studied using medium containing fixed ammonium sulphate concentration of 7.5 $gl^{-1}$ with three different Potassium di hydrogen phosphate levels of 3.5 $gl^{-1}$, 5.25 $gl^{-1}$ and 7 $gl^{-1}$. The chemostat was run at 0.085 dilution rate. The results obtained at three phosphate levels are listed in Table 2. It was observed that increase in phosphate level increased the proteinase A yields in the medium.

TABLE 2

Results of chemostat cultures carried out using S. kluyveri AS57 in medium containing different phosphate levels

| Phosphate levels, g/l | 3.5 | 5.25 | 7 |
|---|---|---|---|
| Dilution rate, $h^{-1}$ | 0.085 | 0.085 | 0.085 |
| Yield of proteinase A, mg/g of biomass | 3.8 | 4.46 | 6.67 |
| Specific proteinase A productivity, mg/g biomass/h | 0.32 | 0.38 | 0.57 |
| Volumetric proteinase A productivity, mg/l/h | 1.55 | 3.07 | 4.82 |

EXAMPLE 3

Investigation on the Effect of Different Ammonium Levels on Proteinase A Production The effect of ammonia present in the fermentation medium on proteinase A production, was investigated in a medium containing fixed potassium dihydrogen phosphate concentration of 3.5 $gl^{-1}$ with three different ammonium sulphate concentrations of 7.5 $gl^{-1}$, 11.5 $gl^{-1}$ and 15 $gl^{-1}$. These studies were carried out at a dilution rate of 0.12 $h^{-1}$. It has been observed that increased level of ammonia increases the proteinase A in the medium when the level of ammonium sulphate was increased from 7.5 $gl^{-1}$ to 11.25 $gl^{-1}$. Further increase in ammonia level resulted in complete absence of proteinase A in extracellular and intracellular medium. This was due to repression of PEP4 expression at this ammonium level. The results are shown in Table 3.

TABLE 3

Results of chemostat cultures carried out using *S. kluyveri* AS57 in medium containing different Ammonium levels

| Ammonium levels, g/l | 7.5 | 11.25 | 15 |
|---|---|---|---|
| Dilution rate, h$^{-1}$ | 0.12 | 0.12 | 0.12 |
| Yield of proteinase A, mg/g of biomass | 4.3 | 6.76 | 0 |
| Specific productivity of proteinase A, mg/g biomass/h | 0.52 | 0.81 | 0 |
| Volumetric productivity of proteinase A, mg/l/h | 3.39 | 6.37 | 0 |

EXAMPLE 4

(1) Studies on Proteinase A Production in Chemostat Cultivation Using Optimised Medium The strain *S. kluyveri* AS57 was tested for proteinase A production in a chemostat culture using the optimised medium with concentrations of Ammonium sulphate (11.25 gl$^{-1}$), and Potassium di hydrogen phosphate (7 gl$^{-1}$) along with other chemicals: trace metals and vitamins. These studies were carried out at two different dilution rates of 0.085 h$^{-1}$ and 0.12 h$^{-1}$. The results are presented in Table 4.

TABLE 4

Performance of *S. kluyveri* AS57 strain in optimized medium

| Dilution rate, h$^{-1}$ | 0.085 | 0.12 |
|---|---|---|
| Yield of biomass, g/g glucose | 0.32 | 0.326 |
| Yield of proteinase A, mg/g of glucose | 6.51 | 10.1 |
| Specific yield, mg/g biomass | 20.12 | 30.9 |
| Specific productivity, mg/g biomass/h | 1.71 | 3.71 |
| Volumetric proteinase A productivity, mg/l/h | 10.67 | 23.35 |

EXAMPLE 5

Construction of an Eexpression Plasmid Coding for an Insulin Precursor MI3

The MI3 insulin precursor is an insulin precursor with the structure B(1-29)-Ala-Ala-Lys-A(1-21) where B(129) is the B chain of human insulin lacking the amino acid residue in position B(30) and A(1-21) is the A chain of human insulin (see EP patent No.163529).

Host strains: *S.kluyveri* ME411=IFO-1894 and *S.cerevisiae* MT663.

Plasmid: pME572, this POT-LEU2 based 2m-pBR322 vector was described of Thim, L. et al, PNAS 83:6766–6770, 1986, where the TPI-promoter-MFa$^{S.c.}$-leader-miniproinsulin-TPI terminator coding sequence was substituted with a MFa$^{S.k.}$-promoter-MFa$^{S.k.}$-leader-M13-TPI$^{S.c.}$ terminator coding sequence. The plasmid also contains the G418$^R$ gene (Kan$^R$). The MI3 part was codon optimized for expression in *S.cerevisiae* according to Egel-Mitani, M. et al. Gene 73:113–120, 1988. The POT-gene is giving strong selection in MT663 on glucose rich media.

Transformed strains: *S.kluyveri* ME578=ME411/pME572 and *S.cerevisiae* ME576=MT663/pME572

Growth media: Agar medium: YG: 1% yeast extract+2% glucose+50 mg G418/l. Liquid culture: ZYM: 2% yeast extract+1% peptone+50 mg G418/l+6% glucose. Gluose was added separately after autoclaving at 121° C., 30 minutes and G418 was sterile filtered before addition to the media.

Liquid growth in shake flasks:

500 ml Erlenmeyer flasks with two bottom casted baffles were filled with 200 ml of ZYM medium. Every flask was inoculated with ¼ of an agar slope. Growth was followed on rotating tables at 250 rpm at 26°, 30° C. and 35° C. Samples were taken after 2 and 3 days of incubation and analyzed for pH, dry biomass and MI3 (HPLC). pH: Carried out on a Radiometer calibrated daily with pH 4,01 and pH 7,01 buffers Dry biomass: Cells were spun down on a Labofuge at 4800 rpm, 5 min. Pellet washed once in deionized water and dried to constant weight in an oven at 105° C. HPLC: The culture broth was diluted 1:1 with a solution of 66% (v/v) ethanol and 0.5% (w/v) of $H_2SO_4$ and kept standing at room temperature for 30 minutes before spinning down at 4800 rpm, 5 minutes. The supernatants were analyzed with the method of Snel, L. and Damgård, U. ("Proinsulin heterogenity in pigs", Horm. Metabolism. Res. 20, 476–488, 1988) with human insulin as an external standard. The results in Table 5 and 6.

TABLE 5

Growth and expression results: Samples after 2 days

| Strain | Temp ° C. | Biomass g/l | pH | Yield HPLC mg/l | Spec. Yield mg/g |
|---|---|---|---|---|---|
| ME576 | 26 | 11.2 | 5.6 | 3.3 | 0.3 |
|  | 30 | 15.7 | 5.1 | 2.9 | 0.19 |
|  | 30 | 18.1 | 5 | 2.5 | 0.14 |
|  | 35 | 15.2 | 5.1 | 0.8 | 00.5 |
| ME78 | 26 | 16.2 | 7.1 | 6.6 | 0.41 |
|  | 30 | 14.2 | 7.1 | 5.9 | 0.41 |
|  | 30 | 14.3 | 7.4 | 3.7 | 0.26 |
|  | 35 | 14 | 5.5 | 9.6 | 0.69 |

TABLE 6

Growth and expression results: Samples after 3 days

| Strain | Temp ° C. | Biomass/l | pH | Yield HPLC mg/l | Spec. Yield mg/g |
|---|---|---|---|---|---|
| ME576 | 26 | 19.9 | 5.2 | 3 | 0.15 |
|  | 30 | 19.2 | 5.3 | <0.6 | <0.03 |
|  | 30 | 16.4 | 5.4 | <0.6 | <0.04 |
|  | 35 | 16.3 | 5.2 | <0.6 | <0.04 |
| ME578 | 26 | 16.0 | 7.7 | 4.4 | 0.28 |
|  | 30 | 13.7 | 7.6 | 5.0 | 0.37 |
|  | 30 | 14.1 | 7.7 | 6.4 | 0.45 |
|  | 35 | 10.1 | 5.4 | 12.2 | 1.21 |

What is claimed is:

1. A method for producing a heterologous product comprising (a) cultivation under industrial conditions a Saccharomyces yeast strain which comprises a plasmid or DNA encoding the heterologous product, wherein the strain utilizes glucose more efficiently and has less fermentative metabolism as compared to that observed in *Saccharomyces cerevisiae* under the same growth conditions, and (b) recovering the heterologous product, wherein the yeast is a naturally occurring Crabtree negative Saccharomyces yeast species.

2. The method according to claim 1, wherein the Crabtree negative Saccharomyces yeast species is *Saccharomyces kluyveri*.

3. The method according to claim 1, wherein the heterologous product is secreted and recovered from the culture medium.

4. The method according to claim 1, wherein the method is a continuous fermentation method.

5. The method according to claim 4, having a dilution rate D higher than $0.2h^{-1}$.

6. The method according to claim 5, wherein the dilution rate is between $0.2h^{-1}$ and $0.5h^{-1}$.

7. The method according to claim 6, wherein the dilution rate is between $0.2h^{-1}$ and $0.3h^{-1}$.

* * * * *